United States Patent
Smith

(10) Patent No.: US 9,030,860 B2
(45) Date of Patent: May 12, 2015

(54) POWER UP DETECTION SYSTEM FOR A MEMORY DEVICE

(71) Applicant: Sidense Corp., Ottawa (CA)

(72) Inventor: Steven Smith, Wakefield (CA)

(73) Assignee: Sidense Corp., Ottawa, Ontario (CA)

( * ) Notice: Subject to any disclaimer, the term of this patent is extended or adjusted under 35 U.S.C. 154(b) by 101 days.

(21) Appl. No.: 13/894,824

(22) Filed: May 15, 2013

(65) Prior Publication Data

US 2013/0308364 A1 Nov. 21, 2013

Related U.S. Application Data

(60) Provisional application No. 61/647,826, filed on May 16, 2012.

(51) Int. Cl.
*G11C 17/00* (2006.01)
*G11C 17/18* (2006.01)
*A61F 13/15* (2006.01)

(52) U.S. Cl.
CPC .......... *G11C 17/18* (2013.01); *A61F 13/15764* (2013.01); *A61F 13/15804* (2013.01)

(58) Field of Classification Search
USPC .......................................................... 365/96
See application file for complete search history.

(56) References Cited

U.S. PATENT DOCUMENTS

| | | | |
|---|---|---|---|
| 5,497,458 A * | 3/1996 | Finch et al. ...................... 714/30 |
| 7,328,388 B2 | 2/2008 | Hii et al. |
| 7,940,595 B2 | 5/2011 | Kurjanowicz |
| 8,023,338 B2 * | 9/2011 | Kurjanowicz ............ 365/189.05 |
| 2009/0051383 A1 * | 2/2009 | Ruf et al. ...................... 324/763 |
| 2010/0011266 A1 * | 1/2010 | Kurjanowicz ................ 714/735 |
| 2011/0317804 A1 * | 12/2011 | Kurjanowicz ................. 377/78 |

FOREIGN PATENT DOCUMENTS

KR 1020080093295 A 10/2008

OTHER PUBLICATIONS

Canadian Patent Application No. 2,815,989, Office Action dated Dec. 5, 2013.
International Patent Application No. PCT/CA2013/050372, International Search Report and Written Opinion dated Aug. 1, 2013.

* cited by examiner

*Primary Examiner* — Hoai V Ho
*Assistant Examiner* — Pablo Huerta
(74) *Attorney, Agent, or Firm* — Jason Mueller-Neuhaus; Borden Ladner Gervais LLP

(57) ABSTRACT

A power up detection method for a memory device and a memory device are disclosed. In a first phase, a test word is read from a read-only memory (ROM) row of a memory array of the memory device, and the test word is compared to predetermined ROM row data. If the test word matches the predetermined ROM row data, a second phase may be performed. In the second phase, first user data is read from a user-programmed row of the memory array at a first time. Second user data is read from the user-programmed row of the memory array at a second time different from the first time. The first user data is compared to the second user data. Successful power up of the memory device is determined when the first user data matches the second user data.

16 Claims, 14 Drawing Sheets

POWER UP DETECTION SYSTEM FOR A MEMORY DEVICE

CROSS REFERENCE TO RELATED APPLICATIONS

This application claims the benefit of priority of U.S. Provisional Patent Application No. 61/647,826 filed on May 16, 2012, which is incorporated herein by reference.

FIELD OF THE INVENTION

The invention is directed to non-volatile memories. More particularly, the invention is directed to verifying power up completion in non-volatile memories.

BACKGROUND OF THE INVENTION

Anti-fuse memory is one type of one-time programmable (OTP) memory in which the device can be permanently programmed (electrically) with data once. This data is programmed by an end user for a particular application. There are several types of OTP memory cells which can be used. OTP memories provide users with a level flexibility since any data can be programmed.

Anti-fuse memory can be utilized in all one time programmable applications where it is desired to provide pre-programmed information to a system, in which the information cannot be modified. One example application includes radio-frequency identification (RFID) tags. RFID tagging applications are gaining more acceptance in the industry, particularly in sales, security, transport, logistics, and military applications for example. The simplicity and full CMOS compatibility anti-fuse memory allows for application of the RFID tag concept to integrated circuit manufacturing and testing processes.

FIG. 1 is a circuit diagram illustrating the basic concept of an anti-fuse memory cell, while FIGS. 2 and 3 show the planar and cross-sectional views respectively, of the anti-fuse memory cell shown in FIG. 1. The memory cell of FIG. 1 includes a pass, or access transistor 10 for coupling a bitline BL to a bottom plate of an anti-fuse device 12. A wordline WL is coupled to the gate of access transistor 10 to turn it on, and a cell plate voltage Vcp is coupled to the top plate of the anti-fuse device 12 for programming the anti-fuse device 12.

It can be seen from FIGS. 2 and 3 that the layout of access transistor 10 and anti-fuse device 12 is very straight-forward and simple. The gate 14 of access transistor 10 and the top plate 16 of anti-fuse device 12 are constructed with the same layer of polysilicon, which extend across active area 18. In the active area 18 underneath each polysilicon layer, is formed a thin gate oxide 20, also known as a gate dielectric, for electrically isolating the polysilicon from the active area underneath. On either side of gate 14 are diffusion regions 22 and 24, where diffusion region 24 is coupled to a bitline. Although not shown, those of skill in the art will understand that standard complementary metal-oxide-semiconductor (CMOS) processing, such as sidewall spacer formation, lightly doped diffusions (LDD) and diffusion and gate silicidation, can be applied. While the classical single transistor and capacitor cell configuration is widely used, a transistor-only anti-fuse cell is further desirable due to the semiconductor array area savings that can be obtained for high-density applications. Such transistor-only anti-fuses must be reliable while simple to manufacture with a low cost CMOS process.

Most systems require a period of time to power up, to ensure that the voltages applied to the components of the system have reached a stable level sufficient to ensure proper operation thereof. There are many known circuits in the art for detecting a voltage supply reaching a predetermined level. However, due to variables such as operating temperature, a simple detection of the supply voltage reaching the predetermined level may not be sufficient for ensuring that the device can properly operate.

It is, therefore, desirable to provide a power up detection system and method which reliably confirms that the OTP memory has completed power up and will thus function as expected.

SUMMARY OF THE DISCLOSURE

The above issues are addressed by embodiments of the invention described herein.

The invention is embodied in a power up detection method for a memory device as follows. A test word is read from a read-only memory (ROM) row of a memory array of the memory device. The test word is compared to predetermined ROM row data. If the test word matches the predetermined ROM row data, the following steps are performed. First user data is read from a user-programmed row of the memory array at a first time. Second user data is read from the user-programmed row of the memory array at a second time different from the first time. The first user data is compared to the second user data. Power up of the memory device is detected when the first user data matches the second user data.

The invention is also embodied in a memory device comprising a memory array, at least one data register, a column decoders and bit line sense amplifier block coupled to the at least one data register for reading data from the memory array into the at least one data register, comparators coupled to the at least one data register, and control logic. The control logic is operative to read by the column decoders and bit line sense amplifier a test word from a read-only memory (ROM) row of the memory array into the at least one data register. The control logic is further operative to compare by the comparators the test word to predetermined ROM row data. The control logic is further operative, if the test word matches the predetermined ROM row data: to read by the column decoders and bit line sense amplifier block first user data from a user-programmed row of the memory array into the at least one data register at a first time; to read by the column decoders and bit line sense amplifier block second user data from the user-programmed row of the memory array into the at least one data register at a second time; to compare by the comparator block the first user data to the second user data; and if the first user data matches the second user data, to enable normal operation of the memory device. The control logic is further operative, if a bit mismatch between the test word and the predetermined ROM row is determined, or if a bit mismatch between the first user word and the second user word is determined, to repeat the power up detection following a predetermined wait period.

Further variants and embodiments are described below.

BRIEF DESCRIPTION OF THE DRAWINGS

Embodiments of the present invention will now be described, by way of example only, with reference to the attached Figures, wherein:

FIG. 4b is a planar layout of the variable thickness gate oxide anti-fuse transistor of FIG. 4a;

FIG. 6 is a schematic of a programmed anti-fuse transistor of FIG. 4a;

DETAILED DESCRIPTION

Generally, the present embodiments are directed to a system and method for determining when a memory device has completed a power up cycle. While the embodiments described below pertain to a non-volatile memory device, and particularly to OTP memory devices wherein the memory cells are anti-fuses, it will be appreciated that the system and method are applicable in any context and to any different type of memory where the characteristics of the non-volatile memory causally related to the functionality and desired results of the system and method are also possessed by the different type of memory. It will further be appreciated that while the embodiments described herein address a dedicated memory device, the described memory array may instead be implemented in a system on a chip (SoC) having embedded memory, or may alternatively be implemented in a memory macro configuration having any appropriate number of macros.

According to some embodiments, application of power to the memory device initiates a first phase of a power up sequence wherein pre-programmed read-only memory (ROM) data of a memory array, the memory device comprising the memory array, is read out and compared to corresponding predetermined bit data. In one embodiment, the corresponding predetermined bit data is hardwired or preconfigured. If the read-out pre-programmed ROM data matches the corresponding predetermined bit data, then in some embodiments a second phase of the power up sequence is executed. In this second phase, certain user-programmed data from the memory array is read out at two different times with an intervening dummy read at a different address location. Thus, the user-programmed data is read out from a first predetermined address at a first time, followed by the intervening dummy read at a different address, and then the user-programmed data is read out from the first predetermined address at a second time. The user-programmed data read out at the first time is compared to the user-programmed data read out at the second time to determine whether they match. In a match condition, power up is considered to be successful—that is, to have completed—and the memory device is then released for normal user operation. Otherwise, if either the first phase or the second phase of the power up sequence fails to return a match result, the entire power up sequence is repeated.

In some embodiments, the memory array comprises memory cells which are anti-fuses, and the user-programmed data read out in the second phase of the power sequence is provided in the memory array by programming corresponding anti-fuse memory cells. The ROM data may be masked programmed or pre-programmed anti-fuses cells, either of which may be done by a manufacturer, and such as not to be directly accessible by a user.

Figure 1:
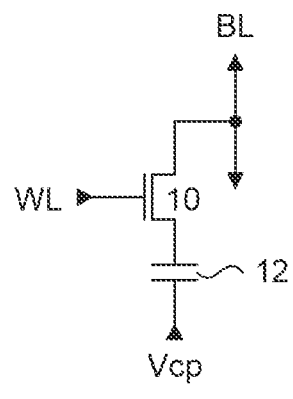
FIG. 1 is a circuit diagram of an anti-fuse memory cell.
Figure 2:
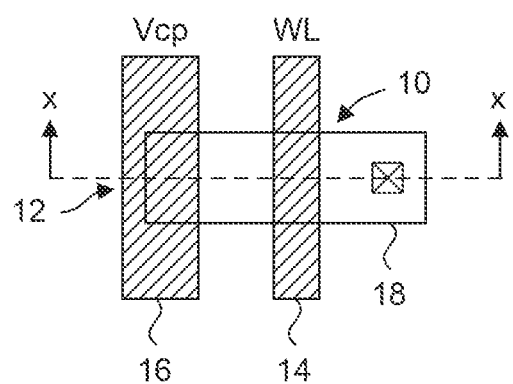
FIG. 2 is a planar layout of the anti-fuse memory cell of FIG. 1.
Figure 3:
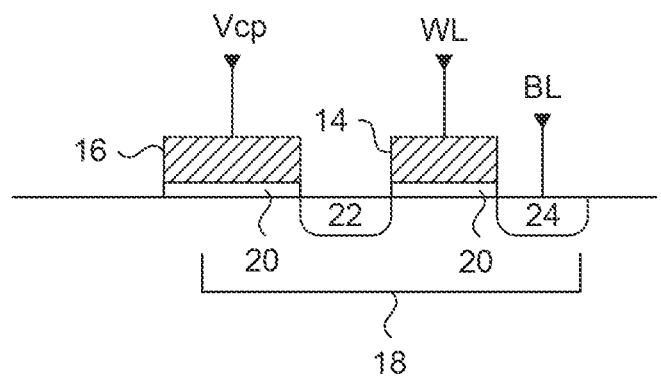
FIG. 3 is a cross-sectional view of the anti-fuse memory cell of FIG. 2 along line x-x.
Figure 4A:
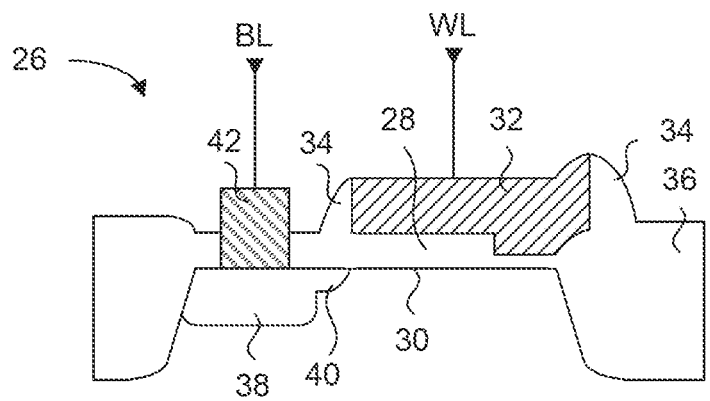
FIG. 4a is a cross-sectional view of a variable thickness gate oxide anti-fuse transistor.

In this connection, FIG. 4a shows a cross-sectional view of an anti-fuse transistor 26 of a memory cell useful for programming the user-programmed data. The anti-fuse transistor 26 can be manufactured with any standard CMOS process. Variants of this anti-fuse transistor 26 are disclosed in commonly owned U.S. Pat. No. 7,755,162, issued on Jul. 13, 2010, the contents of which are incorporated herein by reference. In the presently shown example, the anti-fuse transistor 26 is almost identical to a simple thick gate oxide, or input/output metal-oxide-semiconductor (MOS) transistor with one floating diffusion terminal. The anti-fuse transistor 26, also termed a split-channel capacitor or a half-transistor, can be reliably programmed such that the fuse link between the polysilicon gate and the substrate can be predictably localized to a particular region of the device. The cross-section view of FIG. 4a is taken along the channel length of the device, which in the presently described example is a p-channel device.

Anti-fuse transistor 26 includes a variable thickness gate oxide 28 formed on the substrate channel region 30, a polysilicon gate 32, sidewall spacers 34, a field oxide region 36, a diffusion region 38 and an LDD region 40 in the diffusion region 38. A bitline contact 42 is shown to be in electrical contact with diffusion region 38. The variable thickness gate oxide 28 consists of a thick oxide and a thin gate oxide such that a portion of the channel length is covered by the thick gate oxide and the remaining portion of the channel length is covered by the thin gate oxide. Generally, the thin gate oxide is a region where oxide breakdown can occur. The thick gate oxide edge meeting diffusion region 38 on the other hand, defines an access edge where gate oxide breakdown is prevented and current between the gate 32 and diffusion region 38 is to flow for a programmed anti-fuse transistor. While the distance that the thick oxide portion extends into the channel region depends on the mask grade, the thick oxide portion is preferably formed to be at least as long as the minimum length of a high voltage transistor formed on the same chip.

In this example, the diffusion region 38 is connected to a bitline through a bitline contact 42, or other line for sensing a current from the polysilicon gate 32, and can be doped to accommodate programming voltages or currents. This diffusion region 38 is formed proximate to the thick oxide portion of the variable thickness gate oxide 28. To further protect the edge of anti-fuse transistor 26 from high voltage damage, or current leakage, a resistor protection oxide (RPO), also known as a salicide protect oxide, can be introduced during the fabrication process to further space metal particles from the edge of sidewall spacer 34. This RPO is preferably used during the salicidiation process for preventing only a portion of diffusion region 38 and a portion of polysilicon gate 32 from being salicided. It is well known that salicided transistors are known to have higher leakage and therefore lower breakdown voltage. Thus having a non-salicided diffusion region 38 will reduce leakage. Diffusion region 38 can be doped for low voltage transistors or high voltage transistors or a combination of the two resulting in same or different diffusion profiles.

Figure 4B:
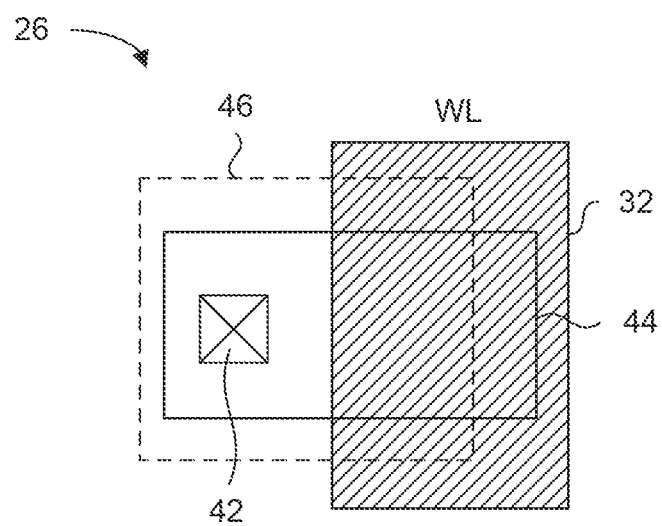

A simplified plan view of the anti-fuse transistor 26 is shown in FIG. 4b. Bitline contact 42 can be used as a visual reference point to orient the plan view with the corresponding cross-sectional view of FIG. 4a. The active area 44 is the region of the device where the channel region 30 and diffusion region 38 are formed, which is defined by an oxide definition (OD) mask during the fabrication process. The dashed outline 46 defines the areas in which the thick gate oxide is to be formed via an OD2 mask during the fabrication process. More specifically, the area enclosed by the dashed outline 46 designates the regions where thick oxide is to be formed. OD simply refers to an oxide definition mask that is used during the CMOS process for defining the regions on the substrate where the oxide is to be formed, and OD2 refers to a second oxide definition mask different than the first. Details of the CMOS process steps for fabricating anti-fuse transistor 26 may be found in above-mentioned U.S. Pat. No. 7,755, 162. According to an embodiment of the present invention, the thin gate oxide area bounded by edges of the active area 44 and the rightmost edge of the OD2 mask, is minimized. In the presently shown embodiment, this area can be minimized by shifting the rightmost OD2 mask edge towards the parallel edge of active area 44. Previously mentioned U.S. Pat. No. 7,755,162 describes alternate single transistor anti-fuse memory cells which can be used in a non-volatile memory array.

Figure 5:
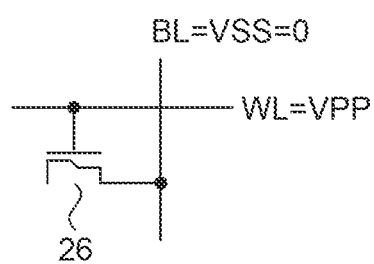
FIG. 5 is a schematic of the anti-fuse transistor of FIG. 4a under programming conditions.
Figure 6:
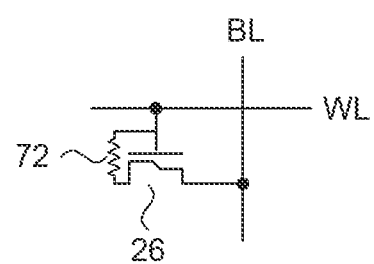

FIG. 5 is a schematic showing the interconnection of the previously described anti-fuse transistor 26 to a bit line and a word line. A successfully programmed anti-fuse transistor 26 is shown in FIG. 6, where a conductive link 72 is formed between the polysilicon gate and the channel region. Conductive link 72 is schematically represented as a resistive connection between the wordline and the channel region under the thin gate oxide region of anti-fuse transistor 26. Therefore a programmed anti-fuse transistor having a conductive link stores one logic state of one bit of data. Accordingly, an unprogrammed anti-fuse transistor will by default store the other logic state of one bit of data. To prevent programming of the anti-fuse transistor 26, the bitline is biased to VDD while the wordline is driven to VPP. This will be sufficient for inhibiting the conductive link from forming.

Figure 7:
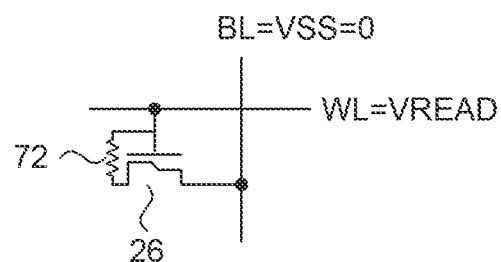
FIG. 7 is a schematic of a programmed anti-fuse transistor of FIG. 4a under read conditions.

Reading the anti-fuse transistor is achieved by driving the wordline to a read voltage VREAD, and by precharging the bitline to VSS, as shown in FIG. 7. If the anti-fuse transistor 26 has a conductive link 72, then the wordline will pull the bitline towards the VREAD voltage level via the conductive link 72 and the positive gate voltage of the anti-fuse transistor. This bitline voltage can be sensed and amplified by sense amplifier circuits. On the other hand, if the anti-fuse transistor 26 is not programmed, ie. does not have a conductive link 72, then the bitline will remain at approximately VSS.

It can therefore be seen that program and read operations should be executed only when the power supply voltages have reached the proper levels. However, it is noted that the purpose of the power up detection cycle is to ensure that the memory device is ready for executing normal operations, such as a read operation by example. In the context of OTP memories by example, it is typically necessary to determine when the memory device is ready for executing read operations. Therefore, the present power up detection embodiments exercise the circuits of the memory device during the power up cycle to determine when a read operation has been successfully executed. In some embodiments, successful execution of at least one read operation is indicative that the memory device has reached a stable power up state and thus can be used for normal operations.

Figure 8:
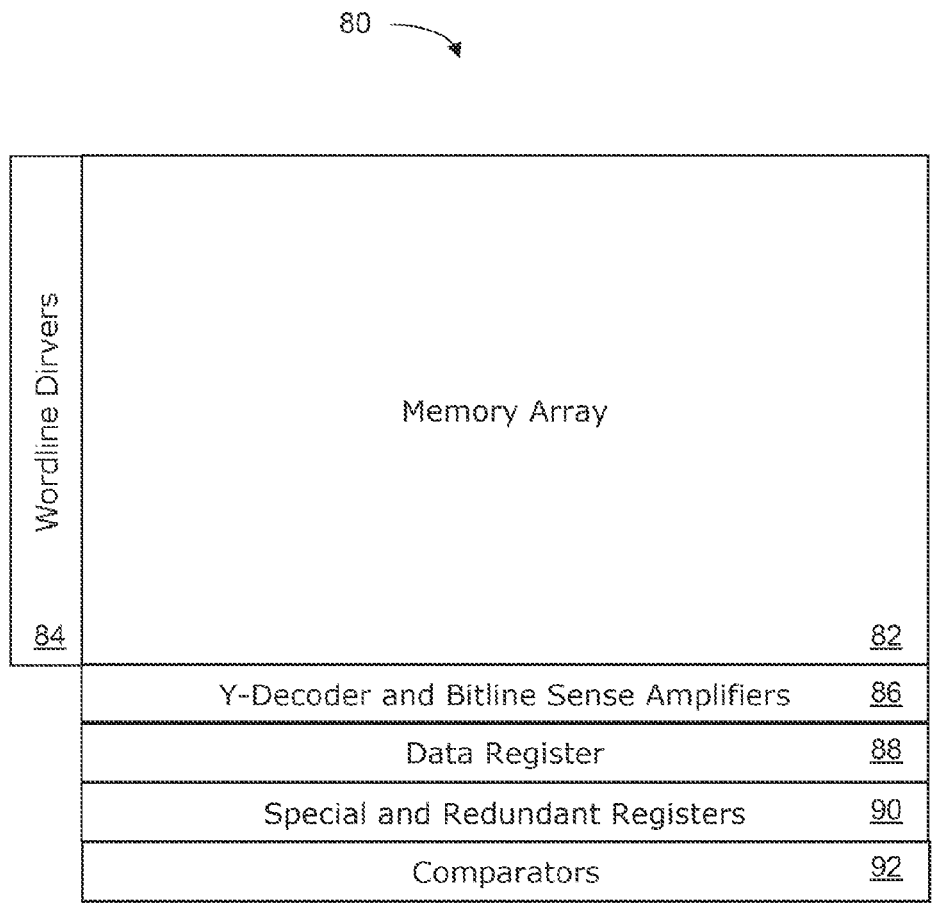
FIG. 8 is a block diagram of a non-volatile memory device having data registers.

FIG. 8 is a block diagram of a memory device 80 (or a macro for an SoC device) and relevant circuits for use in the presently described power up detection embodiments. The memory device includes a memory array 82 comprising OTP memory cells connected to bits lines and word lines. In some embodiments, the OTP memory cells are anti-fuses as described above. The word lines are driven by word line drivers 84 on the left side of the memory array 82, and the bit lines are connected to a column decoders and bit line sense amplifier block 86 located at the bottom of the memory array 82. The column decoder and bit line sense amplifier block 86 is further connected to a primary data register 88, and optionally to special and redundant registers 90. A set of comparators 92 and dedicated logic is included for the presently described power up detection embodiments.

According to some embodiments, the memory array 82 includes at least one row of ROM memory cells connected to the bit lines. Each of the at least one row of ROM memory cells may be mask programmed to store predetermined data. In some embodiments, the remainder of the memory array or at least a portion thereof has been programmed with user data.

The data register 88 is used for storing data to be programmed, or alternatively data provided by the column decoder and bit line sense amplifier block 86 prior to output from the memory device 80 in a read operation. The special and redundant registers 90 may be used for other operations of the memory device 80, such as for example, for redundancy functionality. In all, the memory device 80 includes in some embodiments at least three different registers capable of storing data from the memory array 82. As will be described later, the power up detection embodiments exercise all of the circuits to ensure that they all operate properly during the power up cycle.

Figure 9:
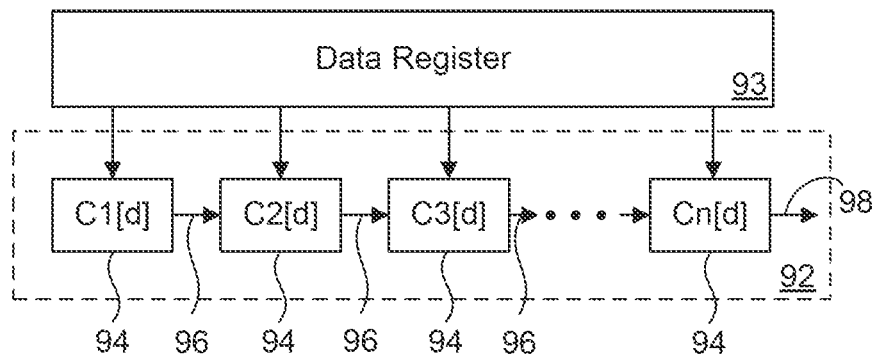
FIG. 9 is a block diagram of a data register connected to bitwise comparators, according to a present embodiment.

FIG. 9 is a block diagram showing a data register 93, which may be the primary data register 88 of FIG. 8, coupled to some of the comparator logic in the comparators block 92 of FIG. 8. It is assumed that the data register 93 stores sensed data from the bit line sense amplifiers in a read operation during the power up cycle. The comparator logic includes a plurality of bitwise comparators 94 "C1[$d$]" to "Cn[d]", where "n" represents the last bit position of the data register, and "d" can represent a logic 0 or 1 value. In some embodiments, "d" is hardwired to have 2 different logic states, wherein the set of first logic states for C1[$d$]" to "Cn[d]" represents one predetermined data word, and the set of second logic states for C1[$d$]" to "Cn[d]" represents another predetermined data word. As will be described later, each of these predetermined data words matches data stored in respective ROM rows of the memory array. In operation during the power up sequence, the data register receives the sensed data corresponding to one of the ROM rows from the bit line sense amplifiers, and each of the bitwise comparators "C1[$d$]" to "Cn[d]" compares the data register data to the corresponding set of logic states to determine if a match is present or not. If the data register receives the sensed data corresponding to the other ROM row, each of the bitwise comparators "C1[$d$]" to "Cn[d]" then compares the data register data to the other set of logic states to determine if a match is present or not.

Each of the bitwise comparators "C1[$d$]" to "Cn[d]" 94 can provide a match result 96 to a following bitwise comparator 94 in a cascading arrangement such that any single bit mismatch results is propagated through to the last bitwise comparator "Cn[d]". The last output 98 therefore indicates if at least one mismatching bit is present.

Figure 10:
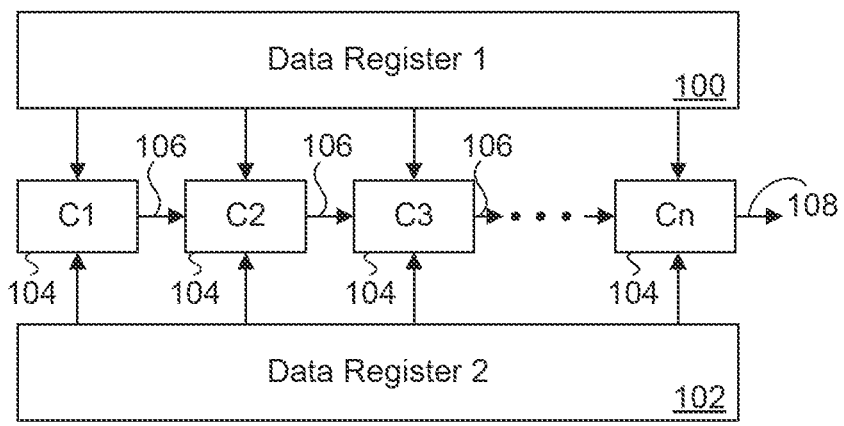
FIG. 10 is a block diagram showing a pair of data registers connected to bitwise comparators, according to a present embodiment.

FIG. 10 is a block diagram showing two data registers 100, 102, which may be the special and redundant data registers 90 of FIG. 8, coupled to some of the comparator logic in the comparators block 92 of FIG. 8. These two registers are simply referred to as "Data Register 1" 100 and "Data Register 2" 102. Both of these data registers may be configured to store sensed data from the bit line sense amplifiers in read operations during the power up cycle. In particular, both of these data registers 100, 102 store user data read from the same row of memory cells of the memory array. The comparator logic includes a plurality of bitwise comparators "C1" to "Cn" 104, where "n" represents the last bit position of the data registers 100, 102. These bitwise comparators 104 are similar to those shown in FIG. 9 except that each bitwise comparator 104 compares data corresponding to the same bit position from both data registers 100, 102 to each other. Once again, cascading logic can be used to pass and combine match/mismatch output information 106 from one bitwise comparator 104 to a subsequent bitwise comparator 104. Accordingly, the contents of both data registers 100, 102 are compared to each other and the last bitwise comparator 104 outputs a result 108 indicating the presence of at least one mismatch, or no mismatch.

Figure 11:
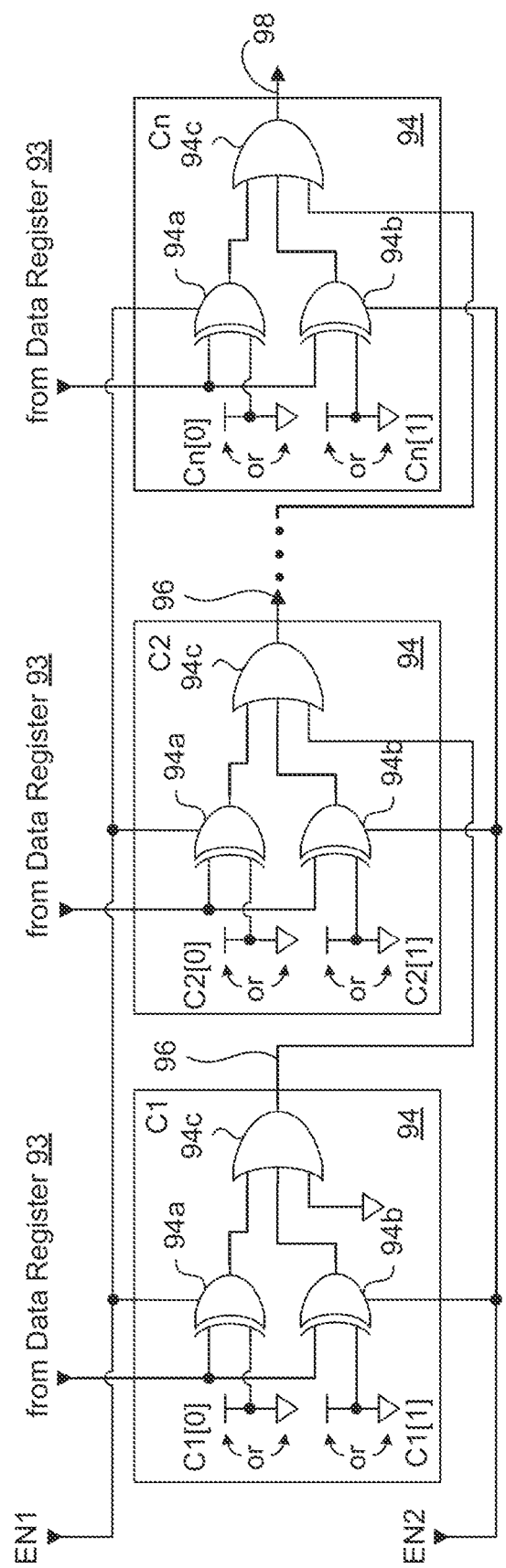
FIG. 11 is a schematic of one embodiment of the bitwise comparators in FIG. 9.
Figure 12:
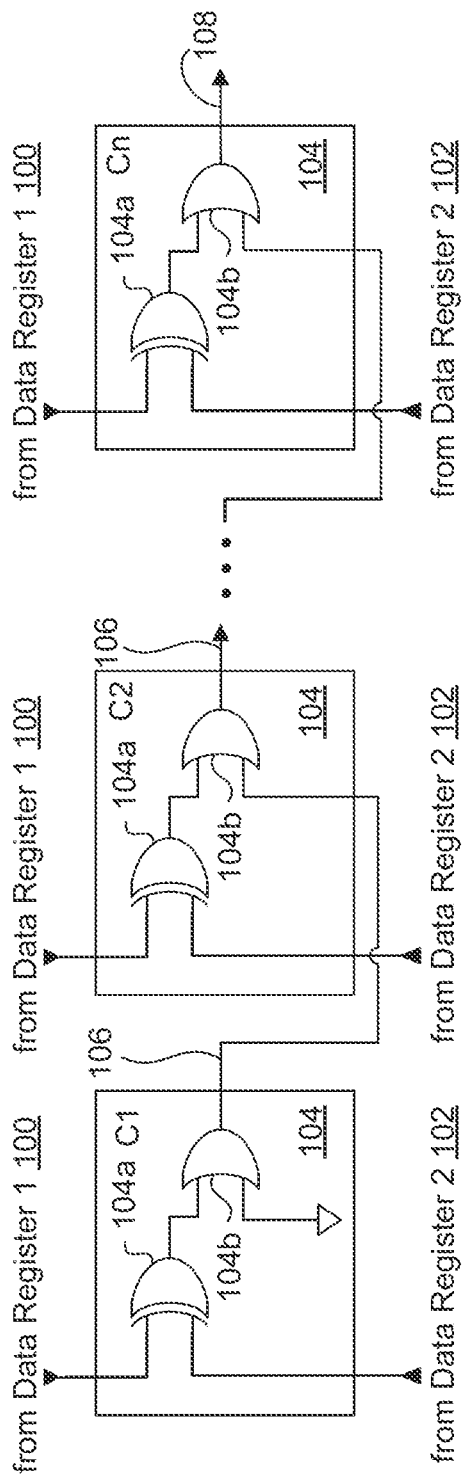
FIG. 12 is a schematic of one embodiment of the bitwise comparators in FIG. 10.

FIGS. 11 and 12 show circuit diagrams, in each case, of one embodiment of the bitwise comparators used in FIGS. 9 and 10. Each comparator 94 includes a first and second XOR logic gates 94a and 94b, and an OR logic gate 94c. The outputs of XOR logic gates 94a and 94b are provided to inputs of OR logic gate 94c, which has a third input for receiving an output from another OR logic gate 94c from a previous comparator 94. In the embodiment of FIG. 11, the left-most comparator 94 is the first, therefore the third input can be tied to VSS, or alternately, a 2-input OR logic gate can be used instead. One input of XOR logic gates 94a and 94b is hardwired to one of two voltage supplies, such as VDD or VSS. The other input of XOR logic gates 94a and 94b receives data from the same corresponding data register.

As shown in FIG. 11, each comparator 94 of the set 92 shown in FIG. 9 may be selectively hardwired with the respective bits of first and second predetermined data words. In this embodiment, selective connection is made either to a logic high, such as VDD, or a logic low, such as VSS, to respective first inputs each of two XOR gates corresponding to the first and second predetermined data words. The second input of each XOR gate receives the sensed data from the corresponding data register 93. Since the mask ROM data is known, each XOR gate input can be appropriately hardwired with the aim of detecting a match with the corresponding read out mask ROM bit from the memory array. The XOR gates 94a used for testing the first predetermined data word are enabled by asserting a first enabling signal EN1, and the XOR gates 94b used for testing the second predetermined data word are enabled by asserting a second enabling signal EN2. As will be apparent from an inspection of the circuit diagram, any mismatch between a sensed ROM row and the corresponding predetermined data word hardwired in the bitwise comparators will be propagated to output 98 via the cascaded, series connected OR logic gates 94c. With this circuit configuration, at least a single bit mismatch can be detected.

Similarly, FIG. 12 shows a circuit diagram of one embodiment of the bitwise comparators 104 shown in FIG. 10. Each comparator 104 includes an XOR logic gate 104a, and an OR logic gate 104b. The output of XOR logic gates 104a is provided to one input of OR logic gate 104b, which has a second input for receiving an output from another OR logic gate 1044 from a previous comparator 104. In the embodiment of FIG. 12, the left-most comparator 104 is the first, therefore the second input can be tied to VSS, or alternately, it can be omitted. Corresponding bits are received from the first and second data registers 100, 102 and are received by corresponding XOR gates 104a. As will be apparent from an inspection of the circuit diagram, any mismatch between the bits received from the first and second data registers will be propagated to output 108 via the cascaded, series connected OR logic gates 104b. With this circuit configuration, at least a single bit mismatch can be detected.

In some embodiments, the memory device 80 is configured to perform a power up detection method as is now described.

Figure 13A:
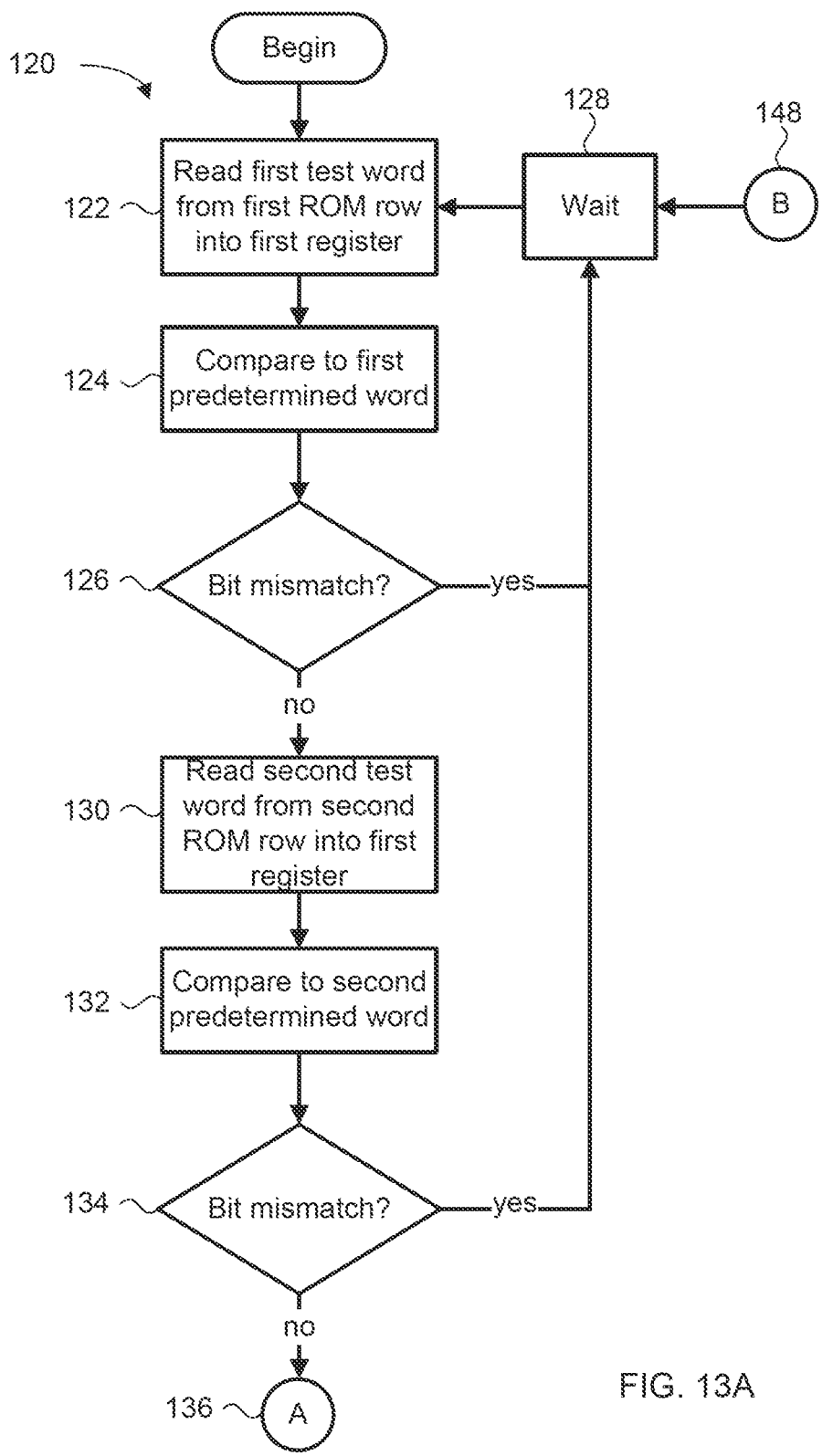
FIGS. 13A, 13B and 13C are flow charts of a power up test method using multiple data registers, according to a present embodiment.

FIG. 13A is a flowchart illustrating a method 120 for power up detection of a memory device. The method starts after a power up detector detects valid voltage levels germane to the operation of the memory device, for example VDD, VCC and VX (read voltage), or after a reset to the memory device. The method starts by reading a first test word from a first ROM row of the memory array and loading the sensed data into a first data register (step 122). Then, the data in the first register is compared to first predetermined ROM row data (step 124). If a single bit mismatches (decision 126), the method loops back to a wait state (step 128). This wait state can be set for any duration of time. Once this duration of time has passed, power up sequence starts over. On the other hand, if there is no bit mismatch and all the respective bits of the first test word and the first predetermined ROM row data match, then the method proceeds to a second read operation where a second test word stored in second ROM row of the memory array is read out and stored in the first register (step 130). Then, the data in the first register is compared to second predetermined ROM row data (step 132). If a single bit mismatches (decision 134), the method loops back to the wait state (step 128) and the power up sequence starts over. Otherwise, if there is no bit mismatch and all the bits match, then a first phase of the power up detector sequence is completed successfully.

In one embodiment, the second ROM row is the first ROM row, and the second ROM row data is the first predetermined ROM row data. In this case, the method confirms the stability or reproducibility of reading from a ROM row. In another embodiment, the second ROM row is different from the first ROM row, and the second predetermined ROM row data is different from the first ROM row data. In this case, the method confirms the reliable reading of variable data from different ROM rows.

Figure 13B:
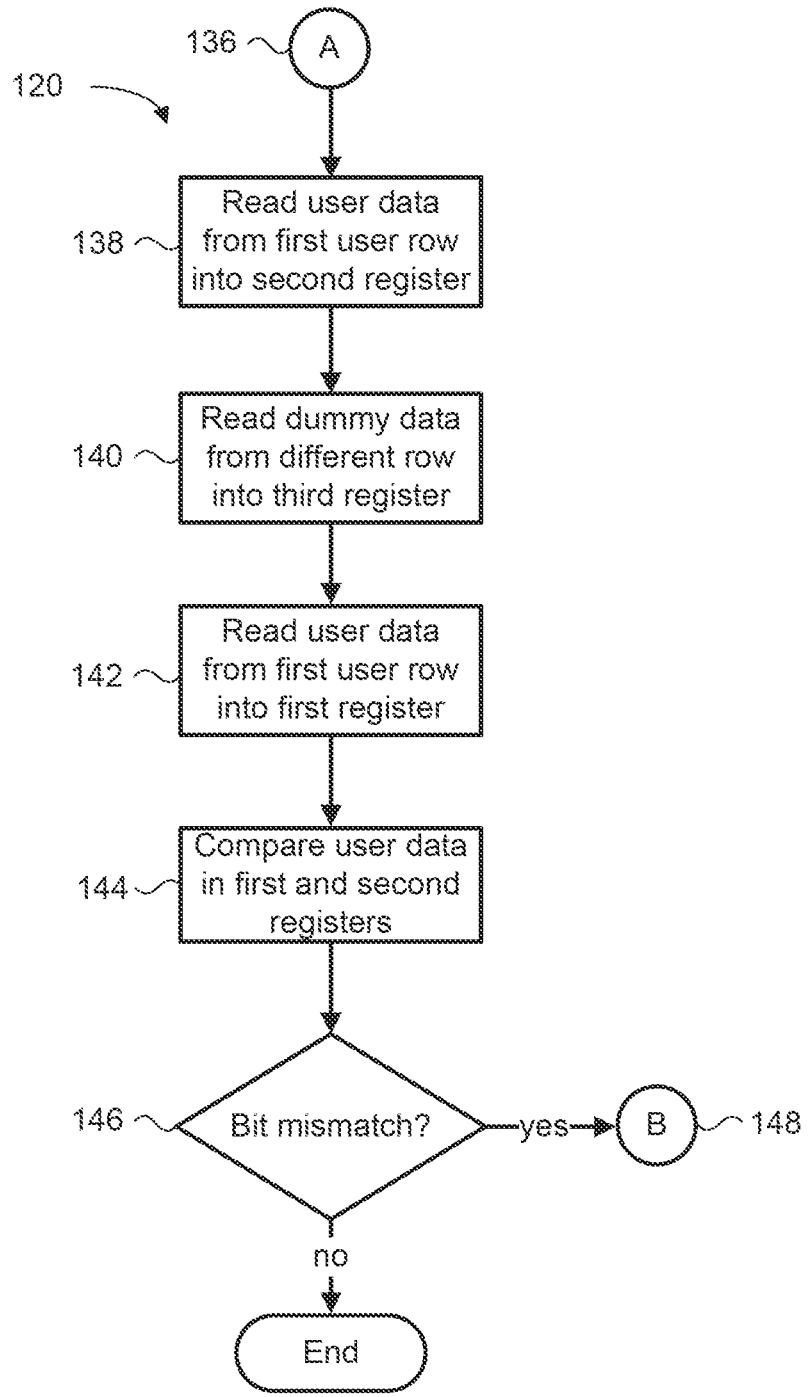

In some embodiments only the first phase described above is performed, and the method 120 ends with the power up sequence being identified as having been successfully completed, thereby indicating that the memory device is ready for use. Normal memory operations may then be enabled. In other embodiments, additional robustness is achieved by also performing the second phase now described. In this case, method 120 continues to the second phase illustrated by the flowchart in FIG. 13B via connector 136.

In the second phase, user data is read from a first predetermined user-programmed row of the memory array and stored into a second register (step 138). In one embodiment, the memory cells are OTP cells, and the user data is thus OTP data. In one embodiment, the OTP cells are anti-fuses. Following this, a dummy read operation may be executed to read user data from a different row, which is stored into a third register (step 140). Then, data from the first predetermined row of the memory array is read again and stored into the first data register (step 142). (It will be appreciated that the particular identity of the first and second data registers is immaterial here, so long as they provide the functionality now described.) Now that the same user data is stored in the second data register and the first data register, a comparison is made between both registers (step 144) to determine if the data stored therein match each other, or if there is even a single bit mismatch (decision 146). If a single bit mismatch occurs, the method returns to the wait state via connector 148 and the entire power up sequence is restarted. Otherwise, if the data in both registers match, then the power up sequence has been successfully completed, thereby indicating that the memory device is ready for use. Normal memory operations may then be enabled.

Figure 13C:
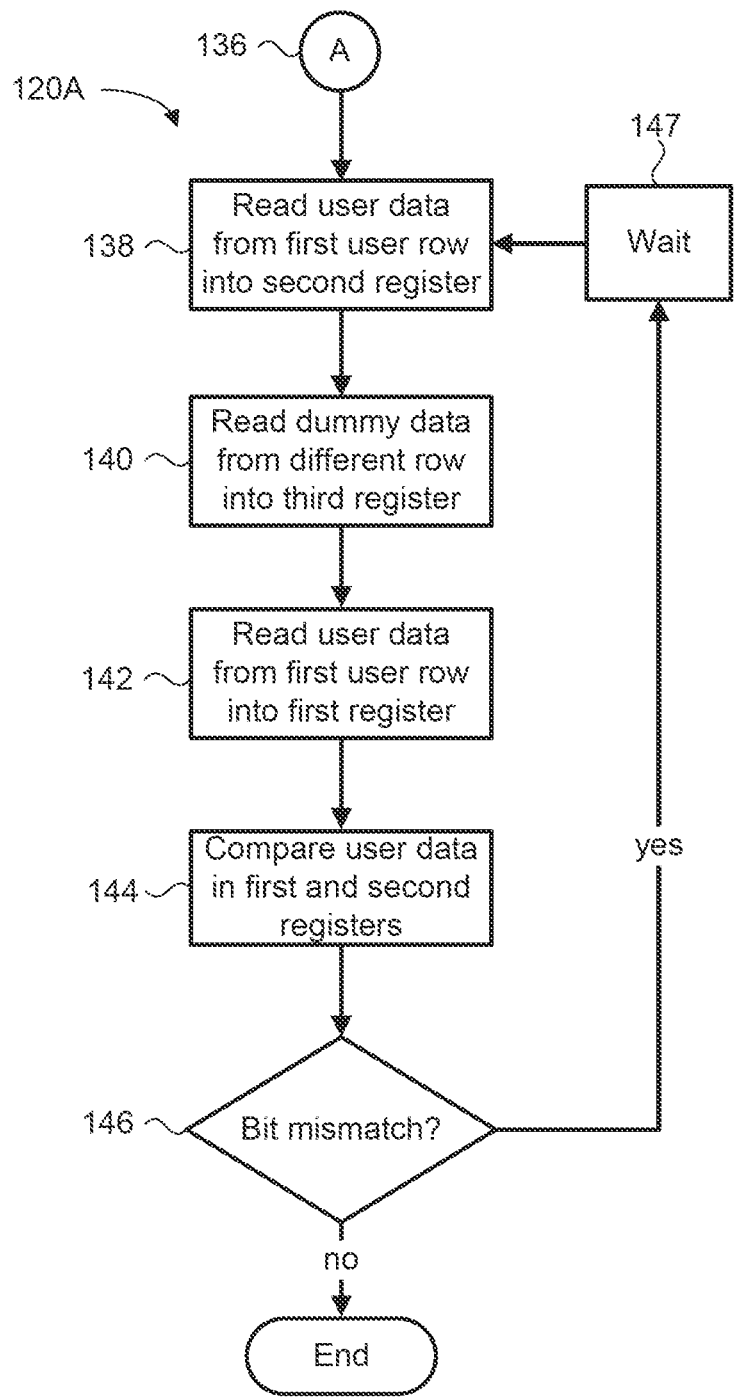

In a variant of the second phase of the method 120 shown in FIG. 13C as method 120A, a bit mismatch (decision 146) does not send the method to the wait state via connector 148, and thence to repeat the first phase shown in FIG. 13A, but instead proceeds to a separate wait state 147 before repeating only the second phase beginning with step 138.

It should be noted that the ROM word stored in the first or second predetermined ROM rows of the memory array can be made more difficult to read than the user programmed OTP data. This can be done by increasing the channel lengths of the ROM cells by example. With reference to FIG. 8, in some embodiments the first register is the data register 88, and the second register is a special register included in the special and redundant registers 90 while the third register is a redundant register included in the special and redundant registers 90. As previously mentioned, not only does the presently described power up sequence determine that read operations can be executed properly, it also confirms that data transfer operations from the data register to the special register or the redundant register can be successfully executed.

The previously disclosed power up detection method uses three data registers available in the memory device. In the event that a memory device does not have three data registers available, the previously disclosed method can be modified for use with a single data register. In this alternative embodiment, a data register is configured to have the ability to store one data word in master latches of each data register stage and another data word in slave latches of each data register stage is used. For example, in a first read operation data is stored in a master latch of each data register stage. Prior to a second read operation, the data stored in the master latches of these data register stage is shifted to a slave latch of each data register stage. Then the second read operation stores data in master latches. Comparison logic can be configured for comparing the data stored in the master and slave latch circuits to each other.

Figure 14A:
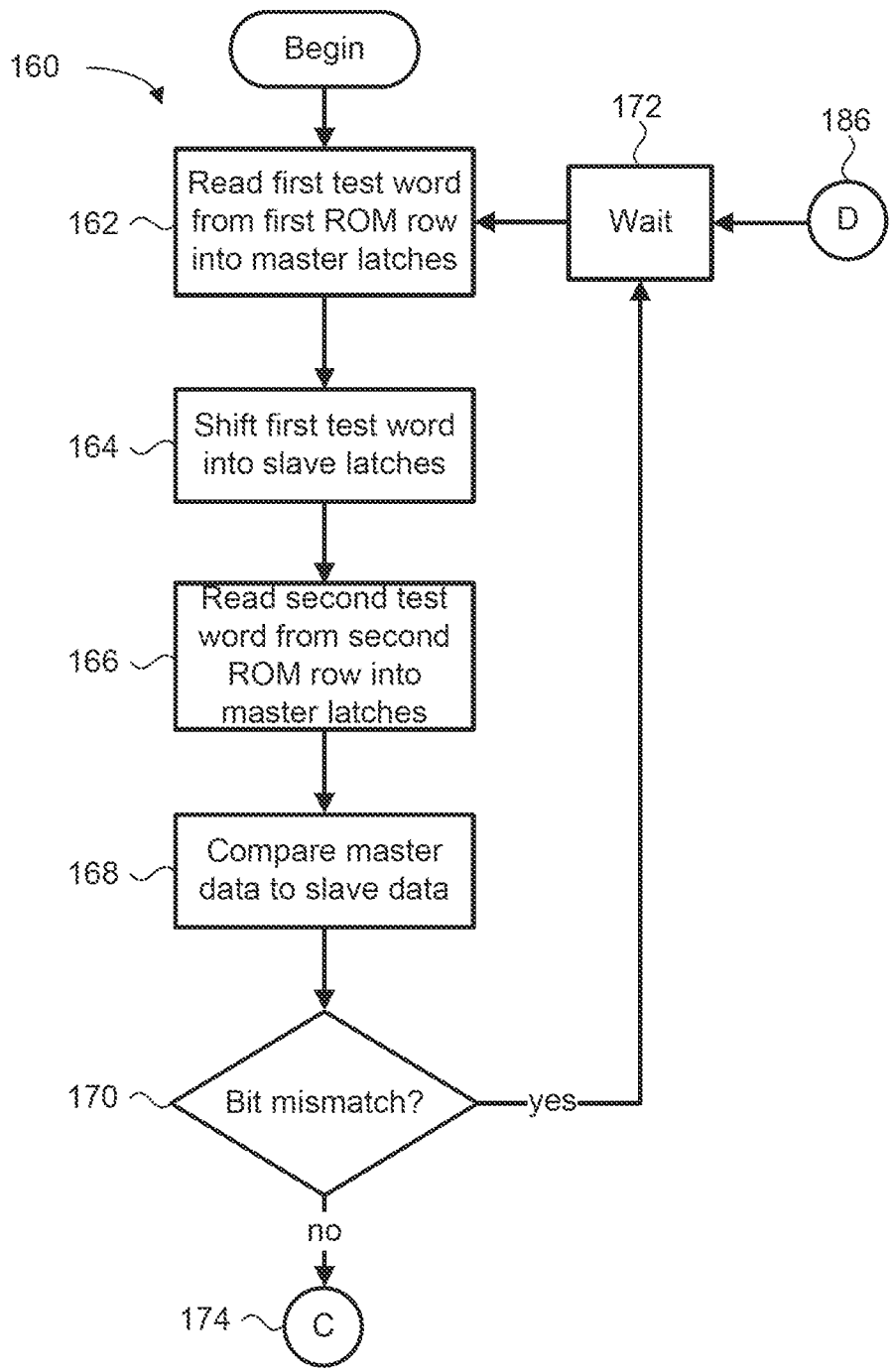
FIGS. 14A, 14B and 14C are flow charts of an alternate power up detection method using a single data register, according to a present embodiment; and, FIG. 15 is a flow chart of a generalized method power up detection method, according to a present embodiment.
Figure 14B:
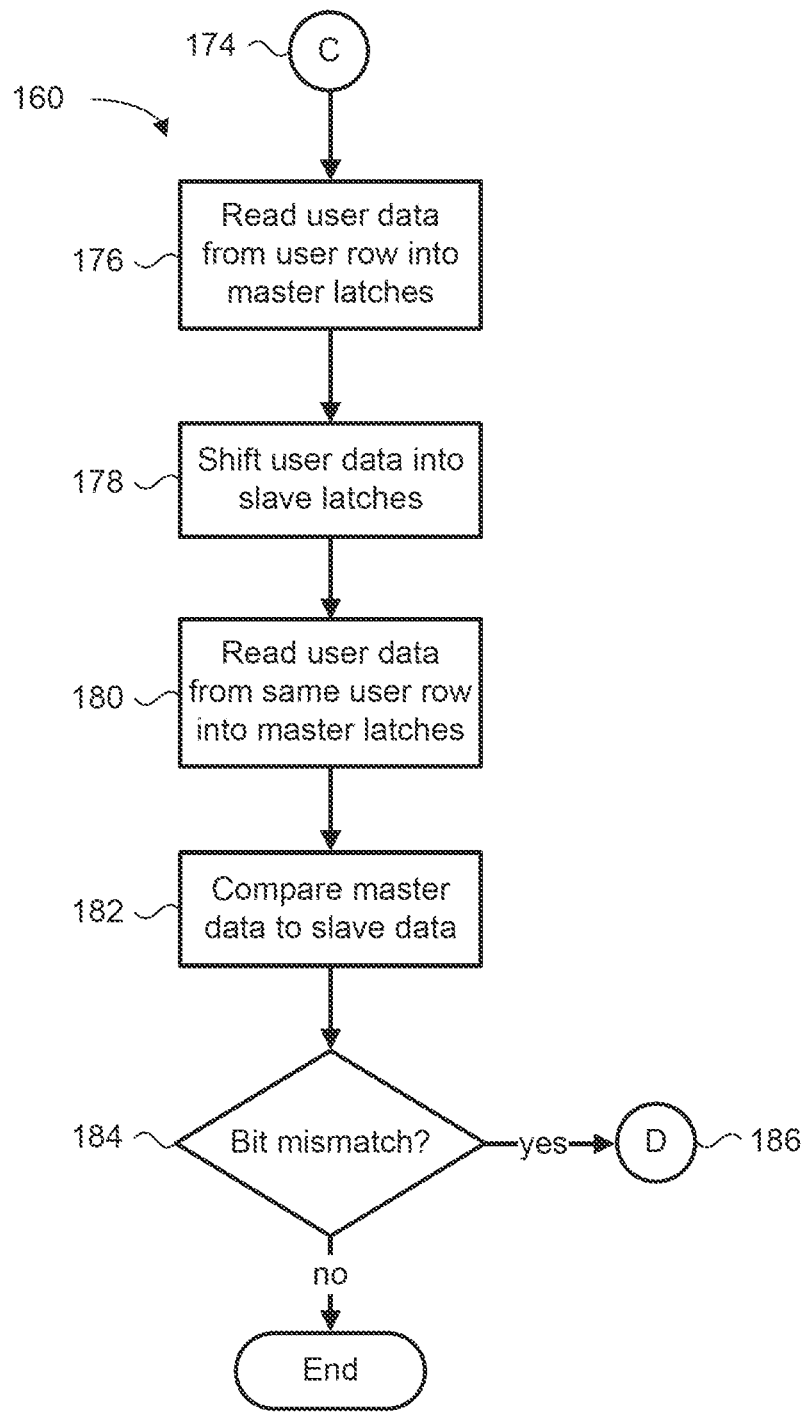

FIG. 14A is a flowchart showing the first phase of an alternative power up detection method 160 using a single data register, such as the aforementioned data register 88, according to a present embodiment. The method starts by reading a first test word from a first ROM row of the memory array and storing the data in the master latches of the data register stages (step 162). Then the data stored in the master latches are shifted to the slave latches (step 164). Following that, the second test word is read from a second ROM row of the memory array into the master latches (step 166). In one embodiment, the first ROM row is preconfigured to contain ROM data identical to ROM data contained in the second ROM row. The data in the master latches are then compared to the data in the slave latches (step 168). If at least one bit mismatches (decision 170), the method proceeds to a wait state (step 172) before restarting the power up detection sequence. Otherwise, all bits match and the method proceeds via connector 174 to a second phase illustrated by the flowchart in FIG. 14B.

In the second phase of the method 160, user data is read from a user row of the memory array into the master latches of the data register (step 176), and shifted to the slave latches (step 178). Data from the same user row is read again and loaded into the master latches (step 180). The data in the master latches are compared to the data in the slave latches (step 182). If a single bit mismatches (decision 184), the method returns to the wait state via connector 186. Otherwise, all bits match thereby indicating successful power up of the memory device.

U.S. Pat. No. 8,023,338, the entirety of which is incorporated herein by reference, describes a power up detection method in which two test words are read from the memory array where the data pattern of one row is shifted by one bit relative to the data pattern of another row. Particular reference is made to FIG. 12 therein. This scheme can be adapted for use with the present embodiments.

Thus, in a variant of the method 160 shown in FIG. 14A, the comparators or other control logic possessed by the memory device are configured to perform a predetermined logical or mathematical operation on at least one of the first and second test words before comparing them. The logical or mathematical operation may be a bit shift such as an arithmetic shift, a logical shift, a rotate no carry (circular shift), or a rotate through carry. Alternatively, the logical or mathematic operation may be at least one predetermined bitwise operator (e.g. NOT, AND, OR, XOR) performed on predetermined bit positions in the first or second test words. In some embodiments, the memory device is provided with a further component, such as logic gates, to perform the logical or mathematical operations.

In such case, the first and second test words may be related by the logical or mathematical operation, and the power up detection method includes transforming a predetermined one of the first and second test words according to the logical or mathematical operation to produce a transformed test word and then comparing the transformed test word with the other one of the first and second test words.

Figure 14C:
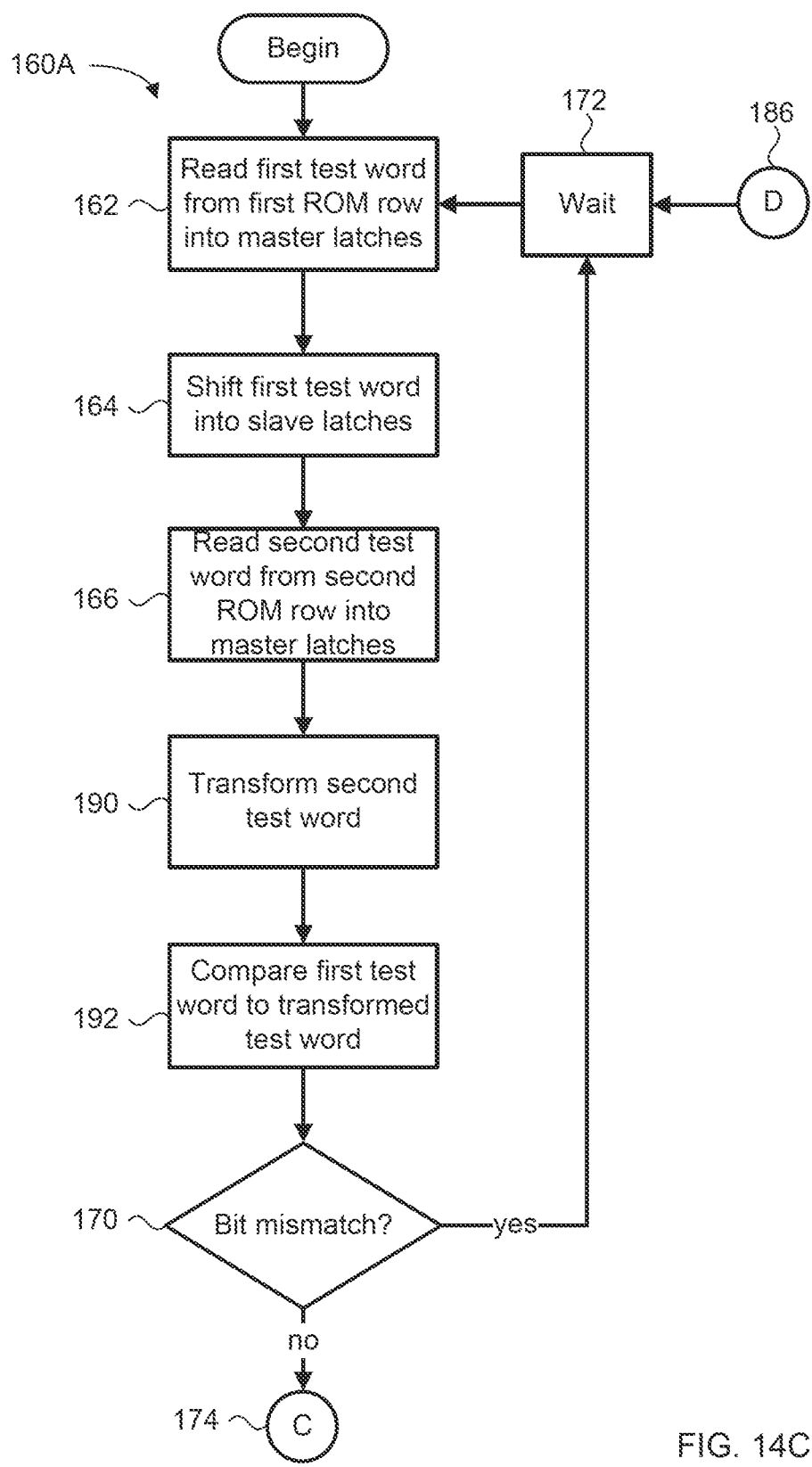

Thus, a variant of the first phase modified accordingly is shown as method 160A in FIG. 14C, wherein the first test word and the second test word are related by some logical or mathematical operation, a further step is performed wherein the comparators or other control logic of the memory device are configured to perform the logical or mathematical operation on the second test word to produce a transformed test word (step 190) prior to comparing the transformed test word with the first test word (step 192). (It will be appreciated that the operation may alternatively be performed on the first test word.) In such case, the transformed test word is expected to be identical to the first test word, and thus following performance of the logical or mathematical operation the comparators are functional to determine whether the transformed test word and first test words match.

In one embodiment, the first test word is read into a master latch of a single register, which is then shifted to a slave latch, the second test word is read into the master latch, the logical or mathematical operation is performed on the data in the master or slave latch, and the respective data in the master and slave latches is then compared. In another embodiment, both the first and second test words are read from user-programmed rows. In another embodiment, one of the first and second test words is read from a ROM row, and the other of the first and second test words is read from a user row.

In another embodiment, the memory device includes multiple data registers wherein the first and second test words are read into different data registers. The transformed test word may be stored in a third data register, or stored in the same data register as the second data register. The comparators may be operative to compare the contents of the different data registers storing the first and transformed test words.

Figure 15:
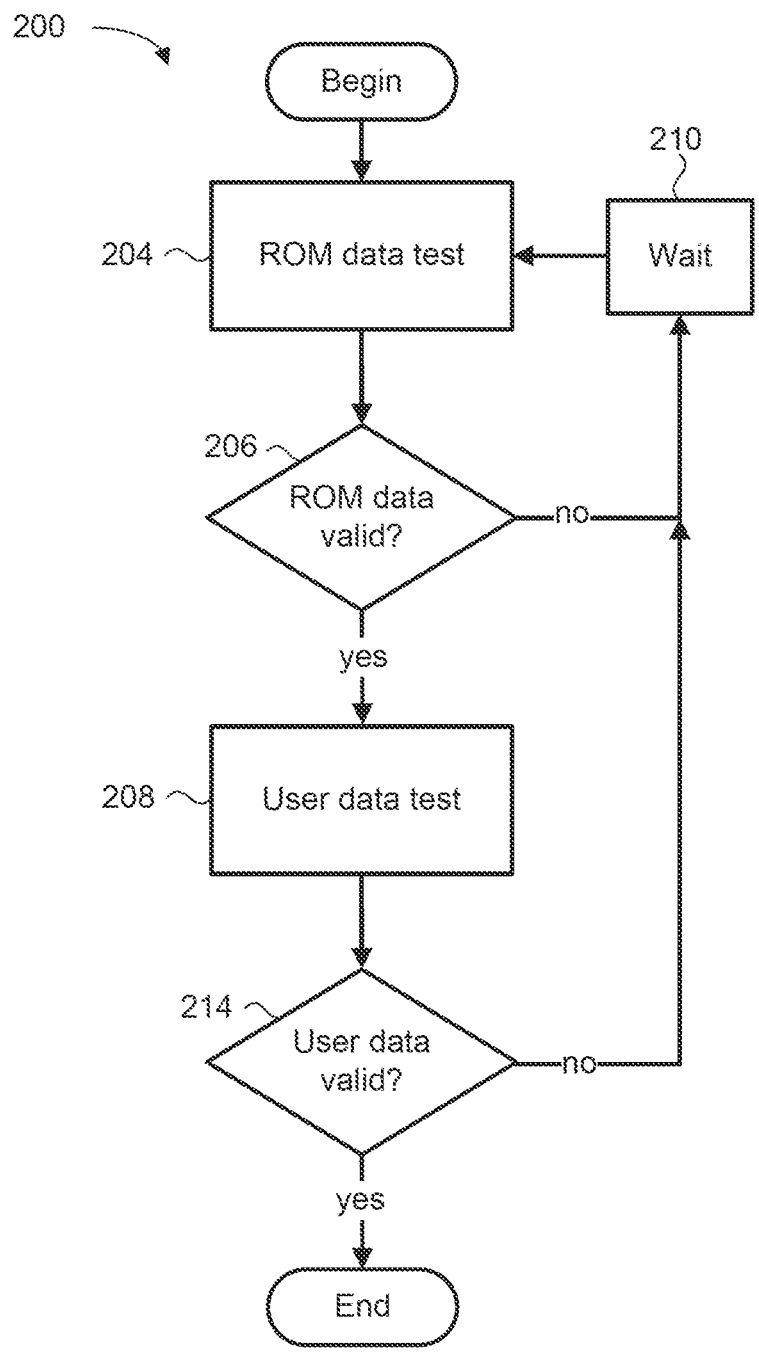

It will thus be appreciated that the above-described methods may be generalized as shown in FIG. 15, and represent embodiments or implementations of the general method 200 shown therein. The general power up method includes two phases of operation. In a first phase a ROM data test is performed at 204. If the ROM data tested is not valid as determined at 206, then the method proceeds to wait for a predetermined duration of time at 210 following which the ROM data test is repeated at 204. According to the present embodiments, the ROM data is determined as being valid when the read out ROM data corresponds to what is expected for a pass condition. The first test phase including 204 and 206 includes 122 to 134 of FIG. 13A, 162 to 170 of FIG. 14A, and 162 to 192 of FIG. 14C.

If the ROM data tested is valid at 206, a second test phase is executed starting at 208, where a user data test is performed. If the user data tested is not valid at 214, then the method proceeds to a wait state 210 for a predetermined duration, following which the ROM data test is repeated at 204. Alternately, a different wait state can be entered after which the method returns to 208 instead. If the user data tested is valid at 214, then the method ends and successful power-up completion is determined. The second test phase including 208 and 214 includes 138 to 146 of FIG. 13B, 138 to 146 of FIG. 13C, and 176 to 184 of FIG. 14B.

It will be appreciated that a memory device described above may be a dedicated memory device or alternatively may be a system on a chip (SoC) device having embedded memory. In alternate embodiments, just one test word from one ROM row is read out before a user data test is executed. In yet other alternate embodiments, more than two test words from two different ROM rows can be read out before a user data test is executed.

In the preceding description, for purposes of explanation, numerous details are set forth in order to provide a thorough understanding of the embodiments of the invention. However, it will be apparent to one skilled in the art that these specific details are not required in order to practice the invention. In other instances, well-known electrical structures and circuits are shown in block diagram form in order not to obscure the invention. For example, specific details are not provided as to whether the embodiments of the invention described herein are implemented as a software routine, hardware circuit, firmware, or a combination thereof.

The above-described embodiments of the invention are intended to be examples only. Alterations, modifications and variations can be effected to the particular embodiments by those of skill in the art without departing from the scope of the invention, which is defined solely by the claims appended hereto.

What is claimed is:

1. A power up detection method for a memory device, the method comprising:
   a) reading a test word from a read-only memory (ROM) row of a memory array of the memory device;
   b) comparing the test word to predetermined ROM row data;
   c) if the test word matches the predetermined ROM row data:
      c.1) reading first user data from a user-programmed row of the memory array at a first time;
      c.2) reading second user data from the user-programmed row of the memory array at a second time different from the first time; and
      c.3) comparing the first user data to the second user data,
   wherein power up of the memory device is detected when the first user data matches the second user data,
   wherein a) comprises reading the test word from the ROM row into a register, and wherein the predetermined ROM row data is preconfigured in a plurality of comparators, wherein b) comprises comparing by the plurality of comparators the test word to the predetermined ROM row data, and
   wherein the test word is a first test word, the ROM row is a first ROM row, the predetermined ROM row data is first predetermined ROM row data, and the plurality of comparators are further preconfigured with second predetermined ROM row data, the method further comprising:
      c.0.1) reading a second test word from a second read-only memory (ROM) row of the memory array of the memory device;
      c.0.2) comparing by the plurality of comparators the second test word to the second predetermined ROM row data; and
      c.0.3) performing c.1) to c.3) only if the second test word matches the second predetermined ROM row data.

2. The power up detection method according to claim 1, wherein the second ROM row is the first ROM row and the second predetermined ROM row data is the first predetermined ROM row data.

3. A power up detection method for a memory device, the method comprising:
   a) reading a test word from a read-only memory (ROM) row of a memory array of the memory device;
   b) comparing the test word to predetermined ROM row data;
   c) if the test word matches the predetermined ROM row data:
      c.1) reading first user data from a user-programmed row of the memory array at a first time;
      c.2) reading second user data from the user-programmed row of the memory array at a second time different from the first time; and
      c.3) comparing the first user data to the second user data,
   wherein power up of the memory device is detected when the first user data matches the second user data,
   wherein the test word is a first test word, and the ROM row is a first ROM row, the method further comprising:
      a.1) reading a second test word from a second ROM row of the memory array of the memory device, the second test word being related to the first test word by a predefined logical or mathematical operation;
      a.2) transforming the second test word based on the predefined logical or mathematical operation thereby to produce a transformed test word, wherein the predetermined ROM row data is the transformed test word.

4. The power up detection method according to claim 3:
   wherein a) comprises reading the first test word into master latches of a register;
   the method further comprising:
      a.0.1) shifting the first test word into slave latches of the register;
   wherein a.1) comprises reading the second test word into the master latches of the register;
   wherein c.1) comprises reading the first user data into the master latches of the register;
   the method further comprising:
      c.1.1) shifting the first user data into the slave latches of the register; and
   wherein c.2) comprises reading the second user data into the master latches of the register.

5. The power up detection method according to claim 3, wherein the predefined mathematical or logical operation is a bit shift or at least one predetermined bitwise operator performed on predetermined bit positions in the second test word.

6. The power up detection method according to claim 5, wherein the bit shift is an arithmetic shift, a logical shift, a rotate no carry (circular shift), or a rotate through carry.

7. A memory device comprising:
a memory array;
at least one data register;
a column decoders and bit line sense amplifier block coupled to the at least one data register for reading data from the memory array into the at least one data register;
comparators coupled to the at least one data register; and
control logic operative:
to read by the column decoders and bit line sense amplifier a test word from a read-only memory (ROM) row of the memory array into the at least one data register;
to compare by the comparators the test word to predetermined ROM row data;
if the test word matches the predetermined ROM row data:
to read by the column decoders and bit line sense amplifier block first user data from a user-programmed row of the memory array into the at least one data register at a first time;
to read by the column decoders and bit line sense amplifier block second user data from the user-programmed row of the memory array into the at least one data register at a second time;
to compare by the comparator block the first user data to the second user data; and
if the first user data matches the second user data, to enable normal operation of the memory device; and
if a bit mismatch between the test word and the predetermined ROM row is determined, or if a bit mismatch between the first user word and the second user word is determined, to repeat the power up detection following a predetermined wait period.

8. The memory device according to claim 7, wherein the user-programmed row comprises one-time-programmed (OTP) memory cells, the first user data comprises first OTP data, and the second user data comprises second OTP data.

9. The memory device according to claim 7, wherein after reading the first user data from the user-programmed row of the memory array into the at least one data register at the first time, and before reading the second user data from the user-programmed row of the memory array into the at least one data register at the second time, the column decoders and bit line sense amplifier block reads dummy user data from a different user-programmed row of the memory array into the at least one data register.

10. The memory device according to claim 9, wherein the at least one data register comprises at least three data registers, wherein the first user data is read into a second data register, the dummy user data is read into a third data register, and the second user data is read into a first data register.

11. The memory device according to claim 9, wherein the comparator block comprises a plurality of comparators, and wherein the predetermined ROM row data is preconfigured in the plurality of comparators.

12. The memory device according to claim 9, wherein the at least one data register comprises a data register having master latches and slave latches, wherein the first user data is read into the master latches, wherein the control logic is further operative to shift the first user data to the slave latches, and wherein the second user data is read into the master latches after the first user data is shifted to the slave latches.

13. The memory device according to claim 7, wherein the test word is a first test word, to ROM row is a first ROM row, and wherein the control logic is further operative:
to read by the column decoders and bit line sense amplifier block a second test word from a second read-only memory (ROM) row of the memory array into the at least one data register, the second test word being related to the first test word by a predefined logical or mathematical operation; and
to transform the second test word based on the predefined logical or mathematical operation thereby to produce a transformed test word, wherein the predetermined ROM row data is the transformed test word.

14. The memory device according to claim 13, wherein the at least one data register comprises a data register having master latches and slave latches, wherein the first test word is read into the master latches, wherein the control logic is further operative to shift the first test data to the slave latches, wherein the second test word is read into the master latches after the first test word is shifted to the slave latches, wherein the first user data is read into the master latches, wherein the control logic is further operative to shift the first user data to the slave latches, and wherein the second user data is read into the master latches after the first user data is shifted to the slave latches.

15. The memory device according to claim 13, wherein the predefined mathematical or logical operation is a bit shift or at least one predetermined bitwise operator performed on predetermined bit positions in the second test word.

16. The memory device according to claim 15, wherein the bit shift is an arithmetic shift, a logical shift, a rotate no carry (circular shift), or a rotate through carry.

* * * * *